US00PP10417P

United States Patent [19]

Jessel, Jr.

[11] Patent Number: Plant 10,417

[45] Date of Patent: May 26, 1998

[54] CARNATION PLANT NAMED 'CFPC PINK MINT'

[75] Inventor: Walter H. Jessel, Jr., Gonzales, Calif.

[73] Assignee: California Florida Plant Co., L. P., Salinas, Calif.

[21] Appl. No.: 749,923

[22] Filed: Nov. 12, 1996

[51] Int. Cl.[6] ..... A01H 5/00

[52] U.S. Cl. ..... Plt./70.2

[58] Field of Search ..... Plt./70.2

*Primary Examiner*—Howard J. Locker

*Attorney, Agent, or Firm*—Christie, Parker & Hale, LLP

[57] ABSTRACT

A new variety of carnation plant producing sprays of pink flushed pale pink flowers.

1 Drawing Sheet

BACKGROUND OF THE INVENTION

The present invention relates to a new and distinct variety of carnation plant which was discovered as a sport in a controlled planting of the cultivar 'CFPC Sugarplum' U.S. Plant Pat. No. 9334. The sport was sectorial, being 2 of 6 flowering shoots. It was reselected and reflowered until stable. The varietal denomination of this new carnation is 'CFPC Pink Mint'.

SUMMARY OF THE INVENTION

The new variety is a true dwarf carnation suitable for growing in 4 to 4½-inch pots (1 plant, 1 pinch, i.e., one plant per pot and one tip pinch on new growth, usually being made 10 to 14 days after planting), tolerant to temperatures of about 10° to 12° F., with a keeping quality of about 3 to 4 weeks. Flower buds open from green bud to maturity with moderate light. No disease problems have been observed as yet.

If planted outdoors, the new variety will continue to recycle growth and blooms. It appears to be perennial in nature in most sections of the country.

In addition to the foregoing, the new variety exhibits superior resistance to soil borne diseases such as *F. oxysporum*, strains 1 and 2, and *F. graminearum*, and root-rots such as damping off, water molds, and the like.

Asexual reproduction by propagation by side shoot cuttings of the new variety as performed in Salinas, Calif., shows that the foregoing and other distinguishing characteristics come true to form and are established and transmitted through succeeding propagations.

Comparison With Parent

The new variety produces pink flowers with a pale pink border or petal edge whereas flowers of its parent, 'CFPC Sugar Plum', are purple with a white border.

BRIEF DESCRIPTION OF ILLUSTRATION

The accompanying illustration shows typical specimens of the flowers and foliage of the new variety depicted in color as nearly true as it is reasonably possible to make the same in a color illustration of this character.

DESCRIPTION OF THE NEW VARIETY

The following is a detailed description of my new variety, with color terminology in accordance with the Royal Horticultural Society Color Chart (R.H.S.C.C.). The terminology used in color description herein refers to plate numbers in the aforementioned color chart. Phenotypic expression and color descriptions may vary depending upon varying environmental, seasonal and cultural conditions.

The information provided herein is based on observations of plants grown inside commercial greenhouses at Salinas, Calif. The height of plant and flower and foliage size are established as an average using standard commercial cultural practices. Where terms such as average, normal, ordinary, etc., are used, the characteristics so described are not considered distinguishing.

Name: 'CFPC Pink Mint'.

Classification:

*Botanical.*—*Dianthus caryophyllus.*

*Commercial.*—Carnation, greenhouse type, suitable for production as a pot variety producing flower sprays.

Parentage: Sport of 'CFPC Sugarplum.'

1. Plant:
   - *Height.*—Pinched plants are about 7 inches tall.
   - *Growing habit.*—Herbaceous, semi-upright.
   - *Blooming habit.*—As a pot spray.
   - *Blooming season.*—Year round.
   - *Rooting time.*—About 18 days.
   - *Mutation prone.*—No.
   - *Disease resistance.*—Good.
   - *Temperature tolerance.*—Wide range.
   - *Breaking action.*—Good, about 5 to 6 lateral shoots per plant.
2. Foliage:
   - *Color.*—Upper side: Near 135A. Lower side: Near 137A.
   - *Size.*—About 3 inches long, about ¼ inches wide.
   - *Quantity.*—Numerous.
   - *Shape.*—Lanceolate.
   - *Texture.*—Smooth.
   - *Ribs.*—Central, keeled.
   - *Arrangement.*—Bi-lateral along stem.
   - *Stem color.*—Green.
3. Bud:
   - *Shape.*—Ovoid.
   - *Color.*—Green.
   - *Length.*—About ⅝ inch.
   - *Diameter.*—About ⅜ inch.
4. Calyx:
   - *Number of sepals.*—About 5.
   - *Length.*—About ⅝ inch.
   - *Width.*—About ¼ inch.
   - *Color.*—Outside — Near 146B. Inside — Near 146D.
5. Bloom:
   - *Shape.*—Round.

*Size.*—Diameter average: About 2 inches. Depth average: About 1 inch.

*Borne.*—As a spray, about 5 to 6 blooms per flowering stem; stem length about 6¾ to 7¾ inches.

*Color.*—General tonality: Pink flushed pale pink. Upper side: Near 66D. Lower side: Near 62B. Center: Near 66D. Outer petals: Whiter than 49D.

*Keeping quality.*—About 3 weeks, majority of flowers on the plant will be spent in about 3 to 4 weeks.

*Fragrance.*—Strong clove scent.

6. Petals:

*Number.*—About 20.

*Outer petals.*—Length: About 1½ inches. Width: About ⅝ inch.

*Central petals.*—Length: About 1¼ inches Width: About ⅜ inch.

*Texture.*—Smooth.

*Form.*—Fan shaped.

*Appearance.*—Shiny, the petal margins are saw-toothed or serrated.

7. Reproductive Organs:

*Stamens.*—None (male sterile).

*Pistil.*—Number: About 1. Color: Base near 155D, remainder near 63A. Length: About 1 inch.

*Stigma.*—Number: About 2. Color: Near 63A.

*Ovary.*—Shape: Conical. Color: Base near 159C. Body near 159C. Apex near 149D.

*Fertility.*—Female: Sterile, abnormal, hair-like, stigmas are very thin and never mature to broadened pubescent structure capable of fecundation where pollen should be applied. Male: Sterile.

I claim:

1. A new and distinct plant variety of carnation plant substantially as shown and described.

* * * * *

PLT-273 SR
C5203 OR PP 010,417
U.S. Patent May 26, 1998 Plant 10,417
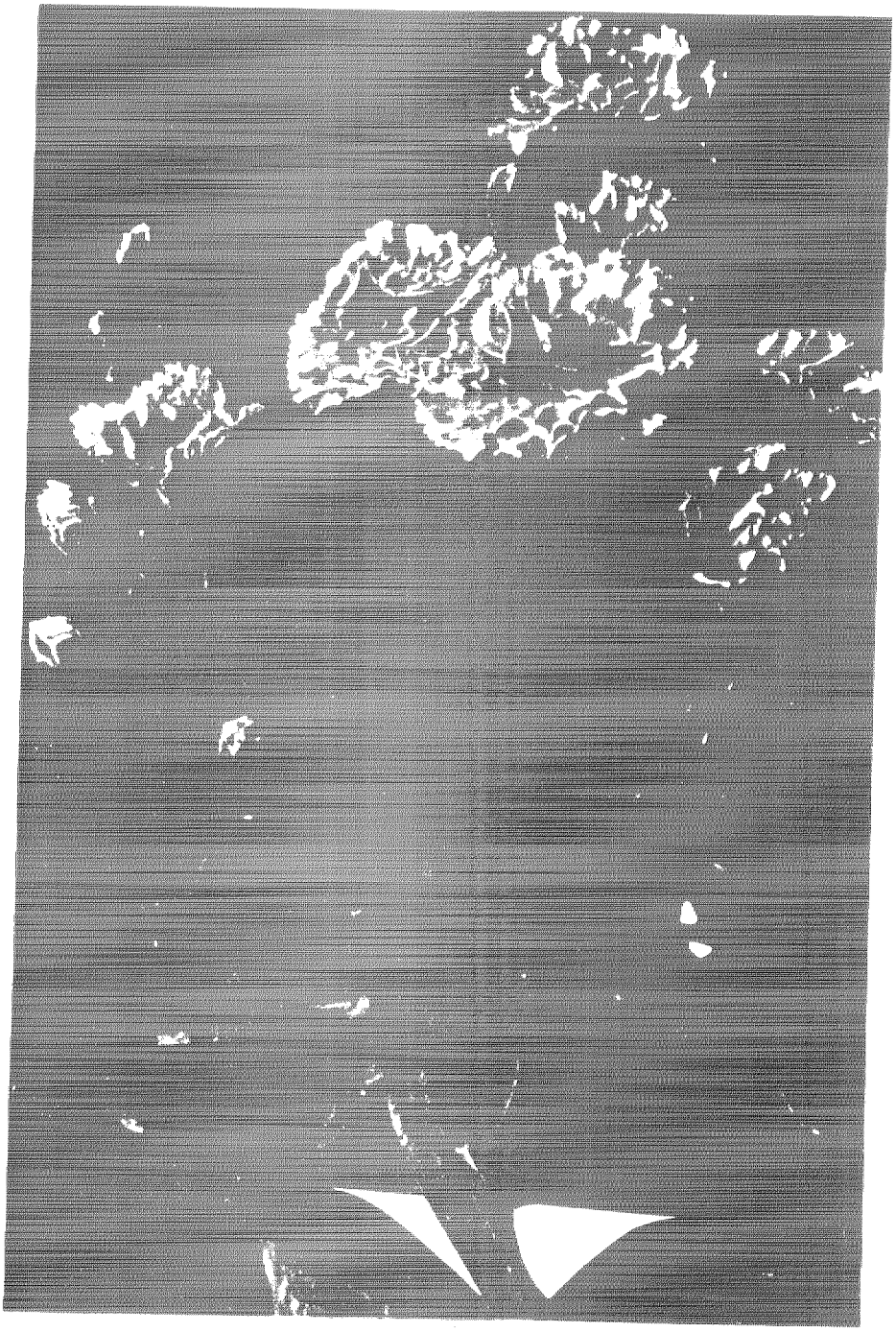

UNITED STATES PATENT AND TRADEMARK OFFICE

CERTIFICATE OF CORRECTION

PATENT NO. : Plant 10,417
DATED : May 26, 1998
INVENTOR(S) : Walter H. Jessel, Jr.

It is certified that error appears in the above-indentified patent and that said Letters Patent is hereby corrected as shown below:

Column 1, line 16, change "12°" to -- 120° --.
Column 1, line 35, replace "pale pink" with -- white --.
Column 2, line 25, replace "Good" with -- Not known --.
Column 3, line 9, replace "spent" with -- dead --.

Signed and Sealed this

Twenty-fourth Day of August, 1999

*Attest:*

Q. TODD DICKINSON

*Attesting Officer*

*Acting Commissioner of Patents and Trademarks*